United States Patent
Powell et al.

(10) Patent No.: US 11,332,794 B2
(45) Date of Patent: May 17, 2022

(54) PROSTATE CANCER AGGRESSIVENESS GENE SIGNATURES FOR SUBJECTS OF AFRICAN OR EUROPEAN DESCENT

(71) Applicant: Wayne State University, Detroit, MI (US)

(72) Inventors: Isaac J. Powell, Detroit, MI (US); Aliccia Bollig-Fischer, Detroit, MI (US); Greg Dyson, Northville, MI (US)

(73) Assignee: Wayne State University, Detroit, MI (US)

( * ) Notice: Subject to any disclaimer, the term of this patent is extended or adjusted under 35 U.S.C. 154(b) by 779 days.

(21) Appl. No.: 16/071,325

(22) PCT Filed: Jan. 19, 2017

(86) PCT No.: PCT/US2017/014142
§ 371 (c)(1),
(2) Date: Jul. 19, 2018

(87) PCT Pub. No.: WO2017/127550
PCT Pub. Date: Jul. 27, 2017

(65) Prior Publication Data
US 2021/0062267 A1 Mar. 4, 2021

Related U.S. Application Data

(60) Provisional application No. 62/280,338, filed on Jan. 19, 2016.

(51) Int. Cl.
*C12Q 1/6886* (2018.01)
*G01N 33/50* (2006.01)

(52) U.S. Cl.
CPC ........ *C12Q 1/6886* (2013.01); *G01N 33/5091* (2013.01); *G01N 2800/7028* (2013.01)

(58) Field of Classification Search
CPC .................... C12Q 1/6886; C12Q 1/68; G01N 2800/7028; G01N 33/5091
See application file for complete search history.

(56) References Cited

FOREIGN PATENT DOCUMENTS

| WO | 2008-079269 A2 | 7/2008 |
| WO | 2015-103166 A1 | 7/2015 |
| WO | 2015-103287 A2 | 7/2015 |

OTHER PUBLICATIONS

Genes associated with prostate cancer are differentially expressed in African American and European American men, 2013, Cancer Epidemiology, Biomarkers & Prevention, vol. 22, No. 5, pp. 891-897. (Year: 2013).*
Powell et al. Cancer Epi Biomarkers Prev (2013) 22(5): 891-897 (Year: 2013).*
Darash-Yahana et al., "Role of high expression levels of CXCR4 in tumor growth, vascularization, and metastasis", (2004) FASEB J : 1-28 (Year: 2004).*
Lipianskaya et al., "Androgen-deprivation therapy-induced aggressive prostate cancer with neuroendocrine differentiation", (2014) Asian J Androl. 16(4): 541-544 (Year: 2014).*
Dutkoski et al., "Protein networks as logic functions in development and cancer", (2011) 7(9):1-11 (Year: 2011).*
Zhang, "Recursive partitioning and tree-based methods", (2004) ECONSTOR: ZBW Papers, No. 2004,30:4-5 (Year: 2004).*
Powell et al., "Genes associated with prostate cancer are differentially expressed in African American and European American men", Cancer Epidemiology, Biomarkers & Prevention, vol. 22, No. 5, pp. 891-897 (May 2013).
Yamoah et al., 'Novel biomarker signature that may predict aggressive disease in African American men with prostate cancer', Journal of Clinical Oncology, vol. 33, No. 25, pp. 2789-2796 (Sep. 1, 2015).

* cited by examiner

*Primary Examiner* — Jehanne S Sitton
*Assistant Examiner* — Daniel W Nielsen
(74) *Attorney, Agent, or Firm* — Julie K. Staple; Dinsmore & Shohl LLP

(57) ABSTRACT

The use of genes or biomarkers to more accurately diagnose aggressive prostate cancer in men of African descent or European descent is provided. More specifically, the genes or biomarkers of the present invention can be used in diagnostic tests and methods to determine, qualify, and/or assess aggressive prostate cancer or status, for example, to diagnose or identify aggressive prostate cancer, in an individual, subject, or patient, such as men of African descent or men of European descent.

9 Claims, 3 Drawing Sheets

PROSTATE CANCER AGGRESSIVENESS GENE SIGNATURES FOR SUBJECTS OF AFRICAN OR EUROPEAN DESCENT

CROSS REFERENCE TO RELATED APPLICATIONS

This application depends from and claims priority to U.S. Provisional Application No. 62/280,338 filed Jan. 19, 2016, the entire contents of which are incorporated by reference.

STATEMENT OF GOVERNMENTAL INTEREST

This invention was made with U.S. government support under grant P30CA022453 awarded by the National Institutes of Health. The U.S. government has certain rights in the invention.

FIELD

The following description relates to the field of gene signatures. More specifically, provided are gene signatures and biomarkers useful in diagnosing or otherwise determining the aggressiveness of prostate cancer in subjects of African or European descent.

BACKGROUND

Prostate cancer is the most common malignancy in men and the second leading cause of death from cancer in the United States second only to lung cancer, killing about 27,540 men each year. About 1 man in 38 will die of prostate cancer. Prostate cancer represents 13.3% of all new cancer cases in the U.S., with about 220,800 new cases of prostate cancer reported each year. About 1 in 7 men will be diagnosed with prostate cancer during their lifetime. The average age at the time of diagnosis is about 66 years old.

The relative 5-year survival rate for prostate cancer is nearly 100%; however, the survival rate for those diagnosed as stage IV with distant metastases is only 28%. Despite more aggressive screening across all demographics and gradual declines in mortality related to prostate cancer in the United States, disparities among populations persist. A substantial proportion of men of African descent have a higher overall incidence, earlier age of onset, increased proportion of clinically advanced disease, and increased bone metastases and mortality from prostate cancer (PCa) compared to men of European descent.

Aggressive prostate cancer leads to a higher metastasis rate and requires early detection and treatment. Since the discovery of prostate-specific antigen (PSA), assays that detect this serum biomarker (together with digital rectal exams) have been used for the screening of prostate cancer. Current initial prostate cancer diagnosis is typically by a prostate biopsy after an abnormal digital rectal exam (DRE) or detection of elevated PSA. PSA testing combined with DRE helps identify prostate cancers at their earliest stages, but studies have disagreed whether these tests reduce the risk of dying of prostate cancer. For that reason, there is debate surrounding prostate cancer screening. If an abnormality is detected on a DRE or PSA test, a physician may recommend tests to determine whether you have prostate cancer, such as ultrasound or biopsy. Although PSA testing has resulted in early detection and intervention, the major limitation of PSA is the low specificity and high prevalence of detecting benign prostatic hyperplasia, especially in older men. Early detection based on PSA testing also fails to distinguish aggressive prostate cancer from non-aggressive prostate cancer. Among men treated for prostate cancer, increasing prostate-specific antigen PSA is known as biochemical failure or biochemical recurrence (BCR). The impact of BCR on subsequent mortality is uncertain, however, especially given competing causes of death. Indeed, with the illustration of the limitations of the current PSA-based screening method, a recently published study randomly assigned 76,693 men at 10 U.S. study centers to receive either annual PSA screening (38,343 subjects) or usual care as the control (38,350 subjects); this study reported no statistical differences in prostate cancer specific mortality between the groups after 7-10 years of follow-up.

The use of PSA screening has resulted in a stage shift to early prostate cancer and in many cases, low risk prostate cancer. There is considerable controversy as to whether "low risk" prostate should be treated. It is increasingly clear that some low risk prostate cancer patients do not progress to aggressive disease and do not need treatment whereas others progress and require treatment; however, it remains difficult to predict which patients will progress from those who will not using histological and clinical characteristics. Currently, there is an increasing use of active surveillance to prevent over-treatment. A study conducted in the state of Michigan by the MUSIC (Michigan Urological Surgery Improvement Collaborative), found that 50% of men with low risk prostate cancer are placed on active surveillance (Womble et al. 2014). Yet there are at least three reports that support caution in including young men of African descent in surveillance, particularly considering that men of African descent are 3-fold more likely than men of European descent to have disease progression. Iremashvili et al. reported that 26% of their patients showed progression at a median of 2.9 year follow up on a mean of 2.3 surveillance biopsies. The progression risk was significantly increased in patients of African descent (adjusted HR 3.87-4.12), and in men with a smaller prostate and higher prostate specific antigen density. They concluded that men of African descent with "low risk" prostate cancer should be advised that the risk of progression on active surveillance many be higher than that in the available literature (Iremashvili et al. 2012). One study reported that men of African descent with very low-risk prostate cancer had more adverse pathologic features at radical prostatectomy and poorer oncologic outcomes (Sundi et al. 2013). Men of African descent were more likely to experience disease upgrading at prostatectomy (27.3% vs 14.4%; P<0.001, positive surgical margins (9.8% vs 5.9%; P=0.02, and higher Cancer of the Prostate Risk Assessment Post-Surgical scoring system (CAPRA-S) scores. On multivariable analysis, the African American race was an independent predictor of adverse pathologic features (odds ratio, [OR] 3.23; P=0.03 and pathologic upgrading (OR, 2.26; P=0.01). Another study reported that African descent was associated with discontinuation of active surveillance for treatment. Men of African descent were associated with treatment (hazard ratio (HR) 2.93, P=0.01) as compared with men of European descent (Abern et al. 2013). When the analysis was adjusted for socio-economic and clinical parameters at the time of prostate cancer diagnosis, men of African descent remained the sole predictor of treatment (HR 3.08, P=0.01). Among men undergoing treatment, the trigger was less often patient driven in men of African descent compared to men of European descent P=0.05 (Abern et al. 2013). As stated earlier, data was reported that prostate cancer grows faster among men of African descent compared to men of European descent. Researchers at Johns Hopkins are reporting long term follow up of racial disparities in oncologic outcomes after radical prostatectomy. In findings using biochemical recurrence (BCR) as an endpoint, men of African descent with very low, low or intermediate risk prostate cancer who undergo radical prostatectomy are more likely to have adverse pathologic findings and BCR compared to men of European descent. Even more important, the data show that BCR-free survival for low risk men of African descent is similar to intermediate risk men of European descent (Faisal A., Schaeffer et al. Oncology, 2014)

Similarly, other current means of prostate cancer risk assessment are also too imprecise to be useful due to determine whether "low risk" prostate patients will progress from those who will not, and thus who should be treated. For example, to determine if a prostate cancer is aggressive (grade), a common scale called the Gleason Score is commonly used. A pathologist microscopically examines a biopsy specimen for certain "Gleason" patterns. These Gleason patterns are associated with the following features:

Pattern 1—The cancerous prostate closely resembles normal prostate tissue. The glands are small, well-formed, and closely packed. This corresponds to a well differentiated carcinoma.

Pattern 2—The tissue still has well-formed glands, but they are larger and have more tissue between them, implying that the stroma has increased. This also corresponds to a moderately differentiated carcinoma.

Pattern 3—The tissue still has recognizable glands, but the cells are darker. At high magnification some of these cells have left the glands and are beginning to invade the surrounding tissue or having an infiltrative pattern. This corresponds to a moderately differentiated carcinoma.

Pattern 4—The tissue has few recognizable glands. Many cells are invading the surrounding tissue in neoplastic clumps. This corresponds to a poorly differentiated carcinoma.

Pattern 5—The tissue does not have any or only a few recognizable glands. There are often just sheets of cells throughout the surrounding tissue. This corresponds to an anaplastic carcinoma.

A pathologist then assigns a grade to the observed patterns of the tumor specimen. A primary grade is assigned to the dominant pattern of the tumor (has to be greater than 50% of the total pattern seen). A secondary grade is assigned to the next-most frequent pattern (has to be less than 50%, but at least 5%, of the pattern of the total cancer observed). The pathologist then sums the pattern-number of the primary and secondary grades to obtain the final Gleason score. If only two patterns are seen, the first number of the score is that of the tumor's primary grade while the second number is that of the secondary grade, as described in the previous section. If three patterns are seen, the first number of the score would be the primary grade and the second number the pattern with the highest grade. However, the risk assessment based on this clinical criterion is too imprecise to be useful due to biopsy sampling error and interobserver grading differences. It is also unable to be used as a non-invasive screening test for early detection of aggressive prostate cancer.

Due to the above mentioned deficiencies in currently available screening methods, aggressive prostate cancer is under detected and under treated while nonaggressive prostate cancer is over detected and over treated. Additionally, the incidence of prostate cancer is 60% greater and the mortality rate is 2 to 3 times higher when comparing men of African descent with men of European descent. Therefore, reliable prostate cancer gene signatures and biomarkers that are differentially present in non-aggressive prostate cancer and aggressive prostate cancer, as well as differentially present in men of African descent and men of European descent, are needed to accurately and reliably distinguish aggressive and nonaggressive prostate cancer in order to prevent patients with nonaggressive prostate cancer from overtreatment and to allow patients with aggressive cancer to receive appropriate treatment earlier in the course of their disease.

SUMMARY

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

One object is to provide methods to accurately and reliably distinguish aggressive and nonaggressive prostate cancer in order to prevent patients with nonaggressive prostate cancer from overtreatment and to allow patients with aggressive cancer to receive appropriate treatment earlier in the course of their disease. This object is achieved in the present disclosure that relates to the use of genes or biomarkers to more accurately diagnose aggressive prostate cancer in men of African descent or European descent. More specifically, the genes or biomarkers of the present invention can be used in diagnostic tests and methods to determine, qualify, and/or assess aggressive prostate cancer or status, for example, to diagnose aggressive prostate cancer, in an individual, subject, or patient, such as men of African descent and men of European descent.

In aspects, a method for identifying a male of African descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; and c) determining the expression threshold level for each prostate cancer driver gene in step b. In aspects, determining the expression threshold level for each gene comprises: 1) measuring the amount or expression of each prostate cancer drive gene in step b or biomarkers in a statistically significant number of samples from male patients of African descent with the different aggressive prostate cancer statuses; and 2) utilizing a defined aggressive phenotype and non-aggressive phenotype of prostate cancer in predicting prostate cancer disease aggressiveness using recursive partitioning; d) determining a number of positive indications for aggressive prostate cancer by comparing the detected expression levels of each gene determined in step b) to the expression threshold level for each determined in step c) for each gene. The method further comprises the steps of: e) determining a gene score threshold using recursive partitioning; and f) identifying the patient as having or likely to have aggressive prostate cancer if there are more positive indications then the gene score threshold determined in step e).

In other aspects, a method for identifying a male of European descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; and c) determining the expression threshold level for each prostate cancer driver gene in step b. In aspects, determining the expression threshold level for each gene comprises: 1) measuring the amount or expression of each prostate cancer drive gene in step b or biomarkers in a statistically significant number of samples from male patients of European descent with the different aggressive prostate cancer statuses; and 2) utilizing a defined aggressive phenotype and non-aggressive phenotype of prostate cancer in predicting prostate cancer disease aggressiveness using recursive partitioning; d) determining a number of positive indications for aggressive prostate cancer by comparing the detected expression levels of each gene determined in step b) to the expression threshold level for each determined in step c) for each gene. The method further comprises the steps of: e) determining a gene score threshold using recursive partitioning; and f) identifying the patient as having or likely to have aggressive prostate cancer if there are more positive indications then the gene score threshold determined in step e).

In further aspects, a method for identifying a male of African descent as having or likely to have aggressive prostate cancer is provided. In some aspects, the methods comprise the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; c) determining a number of positive indications for aggressive prostate cancer by comparing the detected expression levels of each of the prostate cancer driver genes determined in step b to an expression threshold level for each prostate cancer driver gene; and d) identifying the patient as having or likely to have aggressive prostate cancer if there are more positive indications then a gene score threshold.

In other aspects, a method for identifying a male patient of European descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; c) determining a number of positive indications for aggressive prostate cancer by comparing the detected expression levels of each of the prostate cancer driver genes determined in step b to an expression threshold level for each prostate cancer driver gene; and d) identifying the patient as having or likely to have aggressive prostate cancer if there are more positive indications then a gene score threshold.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
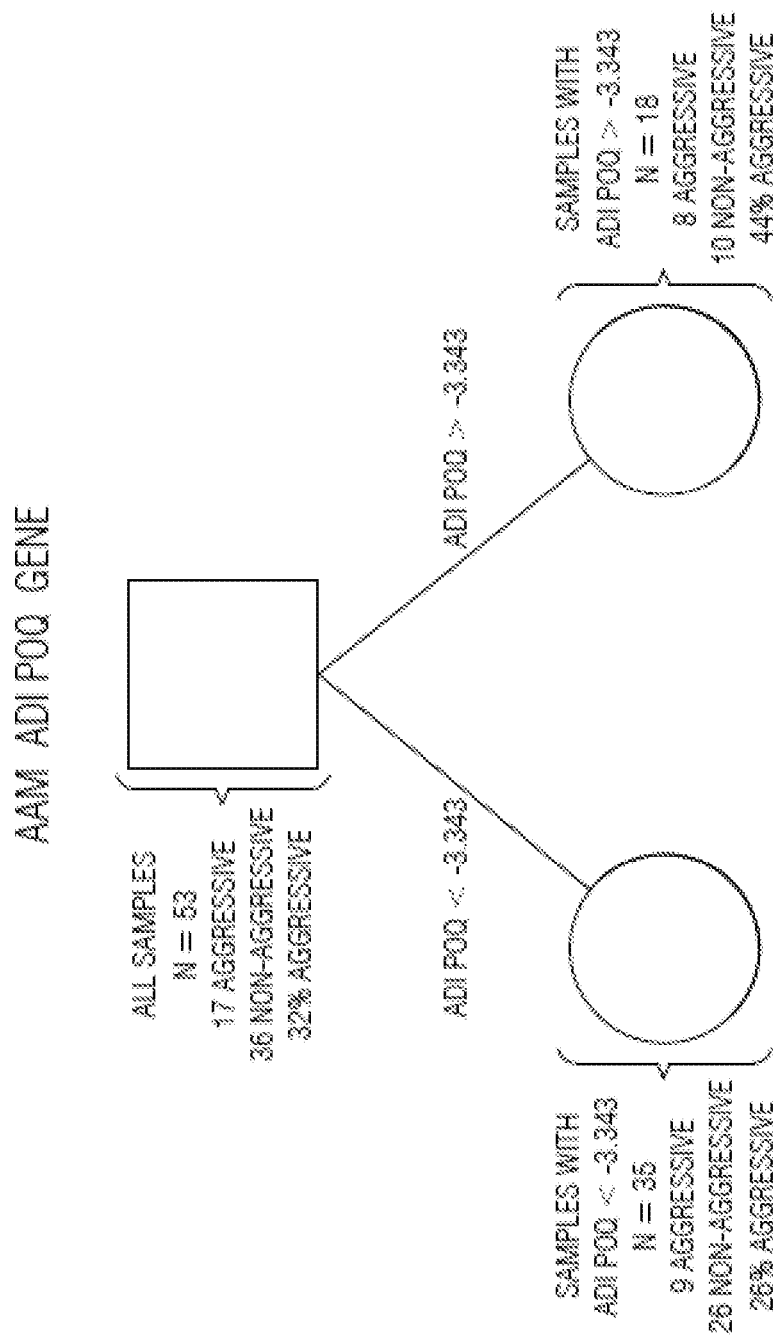
FIG. 1 depicts the method used to determine the expression threshold for ADIPOQ in males of African descent created from the DASL database.

Accordingly, the present disclosure relates to the use of genes or biomarkers to more accurately diagnose aggressive prostate cancer in men of African descent or European descent. More specifically, the genes or biomarkers of the present invention can be used in diagnostic tests and methods to determine, qualify, and/or assess aggressive prostate cancer or status, for example, to diagnose aggressive prostate cancer, in an individual, subject, or patient, such as men of African descent and men of European descent. The genes or biomarkers to be detected in diagnosing aggressive prostate cancer include the following functionally related, prostate cancer driver genes: Adiponectin (ADIPOQ; Entrezgene Accession No. 9370); Rac Protein Kinase Alpha (AKT-1; Entrezgene Accession No. 207); Arachidonate 12-Lipoxygenase (ALOX 12; Entrezgene Accession No. 239); Arachidonate 15-Lipoxygenase (ALOX15; Entrezgene Accession No. 246); Arachidonate 15-Lipoxygenase, Type B (ALOX15B; Entrezgene Accession No. 247); Bone Morphogenetic Protein 2 (BMP2; Entrezgene Accession No. 650); Chorionic Gonadotrophin Subunit Alpha (CGA; Entrezgene Accession No. 1081); C-X-C chemokine receptor type 4 (CXCR4; Entrezgene Accession No. 7852); Cytochrome P450, Family 19, Subfamily A, Polypeptide 1 (CYP19A1 Entrezgene Accession No. 1588); ETS Related Gene (ERG; Entrezgene Accession No. 2078); Fatty Acid Synthase (FASN; Entrezgene Accession No. 2194); Interleukin-1 beta (ILB1; Entrezgene Accession No. 3553); Interleukin 6 (IL6; Entrezgene Accession No. 3569); Interleukin 8 (IL8; Entrezgene Accession No. 3576); Nuclear Factor Of Kappa Light Polypeptide Gene Enhancer In B-Cells 1 (NFKB1; Entrezgene Accession No. 4790); Phosphatidylinositol 3-Kinase, Catalytic Subunit Type 3 (PIK3C3; Entrezgene Accession No. 5289); Phosphatidylinositol-4,5-Bisphosphate 3-Kinase, Catalytic Subunit Alpha (PIK3CA; Entrezgene Accession No. 5290); Phosphoinositide-3-Kinase, Regulatory Subunit 1 (PIK3R1; Entrezgene Accession No. 5295); Phospholipase A2, Group IIA (PLA2G2A; Entrezgene Accession No. 5320); Transforming Growth Factor, Beta 1 (TGFB1; Entrezgene Accession No. 7040); and Tissue Inhibitor Of Metalloproteinases 3 (TIMP3; Entrezgene Accession No. 7078). These genes or biomarkers can be differentially present/expressed in non-aggressive prostate cancer and aggressive prostate cancer, as well as in males of both African and European descent, and are therefore useful in aiding in the accurate determination of aggressive prostate cancer status in these two separate subject cohorts.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

The terminology used herein is for the purpose of describing particular aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "comparing" refers to making an assessment of how the proportion, expression level, or cellular localization of one or more genes or biomarkers of interest in a sample from a subject relates to the proportion, expression level, or cellular localization of the corresponding one or more genes or biomarkers in a standard, reference, or control sample. For example, "comparing" may refer to assessing whether the proportion, expression level, or cellular localization of one or more genes or biomarkers of interest in a sample from a subject, e.g. either African or European descent, is the same as, more or less than, or different from the proportion, expression level, or cellular localization of the corresponding one or more genes or biomarkers in standard, reference or control sample. More specifically, the term may refer to assessing whether the proportion, expression level, or cellular localization of one or more genes or biomarkers in a sample from a patient is the same as, more or less than, different from or otherwise corresponds (or not) to the proportion, expression level, or cellular localization of predefined one or more genes or biomarkers levels/ratios that correspond to, for example, a subject having aggressive prostate cancer, a subject not having aggressive prostate cancer (e.g., non-aggressive prostate cancer or no cancer), a subject that is responding to treatment for aggressive prostate cancer, a subject that is not responding to treatment for aggressive prostate cancer, or a subject that is/is not likely to respond to a particular aggressive prostate cancer treatment. In a specific aspect, the term "comparing" refers to assessing whether the level of the prostate cancer driver genes or biomarkers as provided herein in a sample from a subject is the same as, more or less than, different from other otherwise correspond (or not) to levels/ratios of the same genes or biomarkers in a control sample (e.g., predefined levels/ratios that correlate to unaffected individuals, non-aggressive prostate cancer, standard aggressive prostate cancer levels/ratios, etc.).

As used herein, the terms "identifies," "indicates" or "correlates" (or "identifying," "identification," or "indicating" or "indication" or "correlating," or "correlation," depending on the context) in reference to a parameter, e.g., a gene expression or biomarker level in a sample from a subject, may indicate that the subject has aggressive prostate cancer. In specific aspects, the parameter may include the expression level of one or more genes or biomarkers as provided herein. A particular set or pattern of the expression levels of one or more genes or biomarkers may identify the subject, either of African descent or European descent, as having aggressive prostate cancer (i.e., correlates to a patient having aggressive prostate cancer). In other aspects, a particular set or pattern of the amounts of one or more genes or biomarkers may identify the subject as being unaffected (i.e., indicates a subject does not have aggressive prostate cancer, a subject has non-aggressive prostate cancer, or a patient does not have cancer). In certain aspects, "identifying," "indicating," or "correlating," as used herein, may be by a method of quantifying the relationship between levels/ratios of genes or biomarkers to a standard, control or comparative value for the assessment of the diagnosis, prediction of aggressive prostate cancer or aggressive prostate cancer progression, assessment of efficacy of clinical treatment, identification of a patient that may respond to a particular treatment regime or pharmaceutical agent, monitoring of the progress of treatment, and in the context of a screening assay, for the identification of an anti-aggressive prostate cancer therapeutic.

The terms "patient," "individual," or "subject" can used interchangeably herein, and refer to a mammal, particularly, a human. In certain aspects, the patient may be a male of African descent or a male of European descent. In some aspects, the patient may have mild, intermediate or severe prostate cancer disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" can used interchangeably throughout, and refer to methods which include obtaining a patient sample and/or detecting the expression level of a gene(s) or biomarker(s) in a sample. The terms can also used interchangeably throughout with the term "detecting." In some aspects, the terms refer to obtaining a patient sample and detecting the level of one or more genes or biomarkers in the sample. In other aspects, the terms "measuring" and "determining" mean detecting the level of one or more genes or biomarkers in a patient sample. Measuring can be accomplished by methods known in the art and those further described herein.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient, or a patient having associated symptoms of aggressive prostate cancer. The definition can specifically encompass, e.g. solid tissue samples such as a needle biopsy specimen, e.g. from a prostatectomy, or tissue cultures or cells derived therefrom and the progeny thereof.

Various methodologies as used herein may include a step that involves comparing a value, level, feature, characteristic, property, etc. to a "suitable control," which can be referred to interchangeably as an "appropriate control," a "control sample" or a "reference." A "suitable control," "appropriate control," "control sample" or a "reference" is any control or standard familiar to one of ordinary skill in the art useful for comparison purposes. In some aspects, a "suitable control" or "appropriate control" is a value, level, feature, characteristic, property, etc., determined in a cell, organ, or patient, e.g., a control or normal cell, organ, or patient, exhibiting, for example, normal traits. For example, the genes or biomarkers as used herein may be assayed for levels/ratios in a sample from an unaffected individual or a normal control individual (both terms are used interchangeably herein). In other aspects, a "suitable control" or "appropriate control" is a value, level, feature, characteristic, property, ratio, etc. is determined prior to performing a therapy (e.g., aggressive prostate cancer treatment) on a patient. In yet other aspects, a transcription rate, mRNA level, translation rate, protein level/ratio, biological activity, cellular characteristic or property, genotype, phenotype, etc., can be determined prior to, during, or after administering a therapy into a cell, organ, or patient. In further aspects, a "suitable control," "appropriate control" or a "reference" is a predefined value, level, feature, characteristic, property, ratio, etc. A "suitable control" can be a profile or pattern of levels/ratios of one or more genes or biomarkers as provided herein that correlates to aggressive prostate cancer, to which a patient sample can be compared. The patient sample can also be compared to a negative control, i.e., a profile or pattern of levels/ratios of one or more genes or biomarkers of the present invention that correlates to not having aggressive prostate cancer.

In certain aspects, a "suitable control" can be an expression threshold number for each of the twenty-one functionally related, prostate cancer driver genes or biomarkers disclosed herein by race (males of African descent v. males of European descent) for the specific assay used to measure the gene or biomarker levels/ratios. For example, the presently disclosed methods utilized repeated implementations of a recursive partitioning algorithm to identify subsets of an input dataset with varying levels of a response. In some aspects, it is employed one time to identify binary thresholds of gene expression to classify samples into aggressive and non-aggressive subgroups by race. The number of aggressive subgroups for each individual in the database is summed has to create a gene score. Recursive partitioning is then used to identify an expression threshold for the gene score in predicting disease aggressiveness in either males of African descent or males of European descent. In some aspects, an aggressiveness phenotype (aggressive PCa defined as GS≥8 or 7 (4+3), T3 disease and BCR within 3 years) and a non-aggressive phenotype (non-aggressive PCa defined as GS≥6, T2 disease, and no BCR within 5 years), can be used to identify the expression threshold for each of the twenty-one functionally related, prostate cancer driver gene individually by race (males of African descent v. males of European descent) in predicting prostate cancer disease aggressiveness using recursive partitioning (requiring at least 30% of the sample to be in both of the daughter nodes). This results in an expression threshold number for each gene for each race, and can be used to define a high-risk and a low-risk subset for each gene for each race. Subsequently, the number of genes that a patient has that are high risk, based on comparison of the patient's gene expression compared to the expression threshold number for that particular gene, are summed to create a gene score. Recursive partitioning is again used to define a threshold for the gene score for each race, above which the patient has aggressive prostate cancer and below which the patient does not have aggressive prostate cancer.

The present disclosure relates to the use of biomarkers to diagnose aggressive prostate cancer. More specifically, the biomarkers of the present invention can be used in diagnostic methods and tests to determine, qualify, and/or assess aggressive prostate cancer or status, for example, to diagnose aggressive prostate cancer, in an individual, subject or patient. In particular aspects, aggressive prostate cancer status can include determining a patient's aggressive prostate cancer status, for example, to diagnose aggressive prostate cancer, in an individual, subject or patient. More specifically, the genes or biomarkers to be detected in diagnosing aggressive prostate cancer in men of African descent or men of European descent include the following functionally related, prostate cancer driver genes: Adiponectin (ADIPOQ); Rac Protein Kinase Alpha (AKT-1); Arachidonate 12-Lipoxygenase (ALOX 12); Arachidonate 15-Lipoxygenase (ALOX15); Arachidonate 15-Lipoxygenase, Type B (ALOX15B); Bone Morphogenetic Protein 2 (BMP2); Chorionic Gonadotrophin Subunit Alpha (CGA); C-X-C chemokine receptor type 4 (CXCR4); Cytochrome P450, Family 19, Subfamily A, Polypeptide 1 (CYP19A1); ETS Related Gene (ERG); Fatty Acid Synthase (FASN); Interleukin-1 beta (ILB1); Interleukin 6 (IL6); Interleukin 8 (IL8); Nuclear Factor Of Kappa Light Polypeptide Gene Enhancer In B-Cells 1 (NFKB1); Phosphatidylinositol 3-Kinase, Catalytic Subunit Type 3 (PIK3C3); Phosphatidylinositol-4,5-Bisphosphate 3-Kinase, Catalytic Subunit Alpha (PIK3CA); Phosphoinositide-3-Kinase, Regulatory Subunit 1 (PIK3R1); Phospholipase A2, Group IIA (PLA2G2A); Transforming Growth Factor, Beta 1 (TGFB1); Tissue Inhibitor Of Metalloproteinases 3 (TIMP3), or any combination thereof. These genes or biomarkers can be differentially present/expressed in non-aggressive prostate cancer and aggressive prostate cancer as well as in males of either African or European descent, and are therefore useful in aiding in the accurate determination of aggressive prostate cancer status in these two separate patient cohorts.

Adiponectin (ADIPOQ) encodes a protein hormone that modulates a number of metabolic processes, including glucose regulation and fatty acid oxidation. Adiponectin is typically secreted from adipose tissue (and also from the placenta in pregnancy) into the bloodstream and is very abundant in plasma relative to many hormones. The gene has been implicated in prostate cancerogenesis and it may contribute to the molecular basis for the association between obesity and PC.

Rac Protein Kinase Alpha (AKT-1) is one of 3 closely related serine/threonine-protein kinases (AKT1, AKT2 and AKT3) called the AKT kinase, which regulate many processes including metabolism, proliferation, cell survival, growth and angiogenesis. AKT-1 activates the androgen receptor. Over 100 substrate candidates have been reported so far, but for most of them, no isoform specificity has been reported.

Arachidonate 12-Lipoxygenase (ALOX12) encodes a protein coding gene. ALOX12 also codes for the gene that metabolized saturated fatty acids. Diseases associated with ALOX12 include essential thrombocythemia and atherosclerosis. Among its related pathways are metabolism.

Arachidonate 15-Lipoxygenase (ALOX15) is a protein coding gene, and codes for the gene that metabolizes Omega 6. Diseases associated with ALOX15 include prostate adenocarcinoma and atherosclerosis. Among its related pathways are apoptotic pathways in synovial fibroblasts and metabolism.

Arachidonate 15-Lipoxygenase, Type B (ALOX15B) encodes a member of the lipoxygenase family of structurally related nonheme iron dioxygenases involved in the production of fatty acid hydroperoxides. The encoded protein converts arachidonic acid exclusively to 15S-hydroperoxyeicosatetraenoic acid, while metabolizing linoleic acid less effectively. This gene is located in a cluster of related genes and a pseudogene that spans approximately 100 kilobases on the short arm of chromosome 17.

Bone Morphogenetic Protein 2 (BMP2) plays an important role in the development of bone and cartilage. It is involved in the hedgehog pathway, TGF beta signaling pathway, and in cytokine-cytokine receptor interaction. It is involved also in cardiac cell differentiation and epithelial to mesenchymal transition. BMP-2 and BMP-7 are osteoinductive BMPs: they have been demonstrated to potently induce osteoblast differentiation in a variety of cell types.

Chorionic Gonadotrophin Subunit Alpha (CGA) is the alpha subunit of the four human glycoprotein hormones chorionic gonadotropin (CG), luteinizing hormone (LH), follicle stimulating hormone (FSH), and thyroid stimulating hormone (TSH). These four glycoproteins are dimers consisting of alpha and beta subunits that are associated non-covalently. The alpha subunits of these hormones are identical, however, their beta chains are unique and confer biological specificity. The protein encoded by this gene is the alpha subunit and belongs to the glycoprotein hormones alpha chain family. Two transcript variants encoding different isoforms have been found for this gene.

C-X-C chemokine receptor type 4 (CXCR4) is an alpha-chemokine receptor specific for stromal-derived-factor-1 (SDF-1 also called CXCL12), a molecule endowed with potent chemotactic activity for lymphocytes. CXCR4's ligand SDF-1 is known to be important in hematopoietic stem cell homing to the bone marrow and in hematopoietic stem cell quiescence. Recent evidence demonstrates ubiquitin is also a natural ligand of CXCR4. CXCR4 facilitates the movement of cells within the prostate gland and cells from the prostate to bone on lipid rafts.

Cytochrome P450, Family 19, Subfamily A, Polypeptide 1 (CYP19A1) encodes a member of the cytochrome P450 superfamily of enzymes. The cytochrome P450 proteins are monooxygenases which catalyze many reactions involved in drug metabolism and synthesis of cholesterol, steroids and other lipids. This protein localizes to the endoplasmic reticulum and catalyzes the last steps of estrogen biosynthesis. Mutations in this gene can result in either increased or decreased aromatase activity; the associated phenotypes suggest that estrogen functions both as a sex steroid hormone and in growth or differentiation. Alternative splicing results in multiple transcript variants.

ETS Related Gene (ERG) encodes a protein that is typically mutated in cancer. The ERG protein functions as a transcription regulator. The ETS family regulates embryonic development, cell proliferation, differentiation, angiogenesis, inflammation and apoptosis. ERG can undergo chromosomal translocation in prostate cancer and fuse with TMPRSS-2 (TMPRSS2-ERG) and NDRG-1 NDRG1-ERG). TMPRSS2-ERG, causing ERG overexpression may contribute to the development of androgen-independence, creating unregulated and unorganized tissue.

Fatty Acid Synthase (FASN) encodes a multifunctional protein. Its main function is to catalyze the synthesis of palmitate from acetyl-CoA and malonyl-CoA, in the presence of NADPH, into long-chain saturated fatty acids. In some cancer cell lines, this protein has been found to be fused with estrogen receptor-alpha (ER-alpha), in which the N-terminus of FAS is fused in-frame with the C-terminus of ER-alpha. FASN is also reportedly associated with lethal prostate cancer.

Interleukin-1 beta (ILB1) encodes a cytokine protein. IL-1β is a member of the interleukin 1 family of cytokines. This cytokine is produced by activated macrophages as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis. IL-1β activates MAPK and IL8.

Interleukin 6 (IL6) encodes a cytokine that functions in inflammation and the maturation of B cells. In addition, the encoded protein has been shown to be an endogenous pyrogen capable of inducing fever in people with autoimmune diseases or infections. The protein is primarily produced at sites of acute and chronic inflammation, where it is secreted into the serum and induces a transcriptional inflammatory response through interleukin 6 receptor, alpha. The functioning of this gene is implicated in a wide variety of inflammation-associated disease states, including susceptibility to diabetes mellitus and systemic juvenile rheumatoid arthritis. IL6 indirectly activates the androgen receptor.

Interleukin 8 (IL8) encodes a chemokine produced by macrophages and other cell types such as epithelial cells, airway smooth muscle cells and endothelial cells. Endothelial cells store IL-8 in their storage vesicles, the Weibel-Palade bodies. In humans, the interleukin-8 protein is encoded by the IL8 gene. IL-8 is initially produced as a precursor peptide of 99 amino acids long which then undergoes cleavage to create several active IL-8 isoforms. IL-8, also known as neutrophil chemotactic factor, has two primary functions. It induces chemotaxis in target cells, primarily neutrophils but also other granulocytes, causing them to migrate toward the site of infection. IL-8 also induces phagocytosis once they have arrived. IL-8 is also known to be a potent promoter of angiogenesis. In target cells, IL-8 induces a series of physiological responses required for migration and phagocytosis, such as increases in intracellular Ca2+, exocytosis (e.g. histamine release), and the respiratory burst. IL8 indirectly activates the androgen receptor.

Nuclear Factor Of Kappa Light Polypeptide Gene Enhancer In B-Cells 1 (NFKB1) encodes a 105 kD protein which can undergo cotranslational processing by the 26S proteasome to produce a 50 kD protein. The 105 kD protein is a Rel protein-specific transcription inhibitor and the 50 kD protein is a DNA binding subunit of the NF-kappa-B (NFKB) protein complex. NFKB is a transcription regulator that is activated by various intra- and extra-cellular stimuli such as cytokines, oxidant-free radicals, ultraviolet irradiation, and bacterial or viral products. Activated NFKB translocates into the nucleus and stimulates the expression of genes involved in a wide variety of biological functions. Inappropriate activation of NFKB has been associated with a number of inflammatory diseases while persistent inhibition of NFKB leads to inappropriate immune cell development or delayed cell growth. Two transcript variants encoding different isoforms have been found for this gene. NFKB1 activates the androgen receptor directly.

Phosphatidylinositol 3-Kinase, Catalytic Subunit Type 3 (PIK3C3) encodes a catalytic subunit of the PI3K complex that mediates formation of phosphatidylinositol 3-phosphate which plays a key role in initiation and maturation of autophagosomes. Involved in the transport of lysosomal enzyme precursors to lysosomes. Required for the abcission step in cytokinesis. Required for transport from early to late endosomes.

Phosphatidylinositol-4,5-Bisphosphate 3-Kinase, Catalytic Subunit Alpha (PIK3CA) encodes protein that phosphorylates PtdIns (Phosphatidylinositol), PtdIns4P (Phosphatidylinositol 4-phosphate) and PtdIns(4,5)P2 (Phosphatidylinositol 4,5-bisphosphate) to generate phosphatidylinositol 3,4,5-trisphosphate (PIP3). PIP3 plays a key role by recruiting PH domain-containing proteins to the membrane, including AKT1 and PDPK1, activating signaling cascades involved in cell growth, survival, proliferation, motility and morphology. Participates in cellular signaling in response to various growth factors. Involved in the activation of AKT1 upon stimulation by receptor tyrosine kinases ligands such as EGF, insulin, IGF1, VEGFA and PDGF. Involved in signaling via insulin-receptor substrate (IRS) proteins. Essential in endothelial cell migration during vascular development through VEGFA signaling, possibly by regulating RhoA activity. Required for lymphatic vasculature development, possibly by binding to RAS and by activation by EGF and FGF2, but not by PDGF.

Phosphoinositide-3-Kinase, Regulatory Subunit 1 (PIK3R1) encodes a protein that binds to activated (phosphorylated) protein-Tyr kinases, through its SH2 domain, and acts as an adapter, mediating the association of the p110 catalytic unit to the plasma membrane. Necessary for the insulin-stimulated increase in glucose uptake and glycogen synthesis in insulin-sensitive tissues. The protein plays an important role in signaling in response to FGFR1, FGFR2, FGFR3, FGFR4, KITLG/SCF, KIT, PDGFRA and PDGFRB. Likewise, the protein plays a role in ITGB2 signaling (PubMed:17626883, PubMed:19805105, PubMed:7518429), and modulates the cellular response to ER stress by promoting nuclear translocation of XBP1 isoform 2 in a ER stress- and/or insulin-dependent manner during metabolic overloading in the liver and hence plays a role in glucose tolerance improvement.

Phospholipase A2, Group IIA (PLA2G2A) encodes a protein that is a member of the phospholipase A2 family (PLA2). PLA2s constitute a diverse family of enzymes with respect to sequence, function, localization, and divalent cation requirements. This gene product belongs to group II, which contains secreted form of PLA2, an extracellular enzyme that has a low molecular mass and requires calcium ions for catalysis. It catalyzes the hydrolysis of the sn-2 fatty acid acyl ester bond of phosphoglycerides, releasing free fatty acids and lysophospholipids, and thought to participate in the regulation of the phospholipid metabolism in biomembranes. Several alternatively spliced transcript variants with different 5' UTRs have been found for this gene.

Transforming Growth Factor, Beta 1 (TGFB1) encodes a member of the transforming growth factor beta (TGFB) family of cytokines, which are multifunctional peptides that regulate proliferation, differentiation, adhesion, migration, and other functions in many cell types. Many cells have TGFB receptors, and the protein positively and negatively regulates many other growth factors. The secreted protein is cleaved into a latency-associated peptide (LAP) and a mature TGFB1 peptide, and is found in either a latent form composed of a TGFB1 homodimer, a LAP homodimer, and a latent TGFB1-binding protein, or in an active form composed of a TGFB1 homodimer. The mature peptide may also form heterodimers with other TGFB family members. This gene is frequently upregulated in tumor cells, and mutations in this gene result in Camurati-Engelmann disease. TGFB-1 is an androgen responsive element.

Tissue Inhibitor of Metalloproteinases 3 (TIMP3) encodes proteins that are inhibitors of the matrix metalloproteinases, a group of peptidases involved in degradation of the extracellular matrix (ECM). Expression of this gene is induced in response to mitogenic stimulation and this netrin domain-containing protein is localized to the ECM. Mutations in this gene have been associated with the autosomal dominant disorder Sorsby's fundus dystrophy.

In the methods and kits provided herein, the expression level of these functionally related, prostate cancer driver genes or biomarkers are detected. Expression level of a gene is optionally detected by determination of the amount of mRNA expressed by the gene. Optionally, the expression level of a biomarker is detected by the expression level of a protein encoded by a gene. Optionally, a biomarker is detected by the activity of a gene, RNA, or protein toward a substrate, including partner, or other method recognized in the art.

Thus, these functionally related, prostate cancer driver genes and biomarkers provided above can be assayed from a patient sample (e.g. a needle biopsy from a tumor) in diagnostic tests, illustratively through a multiplex assay, to assess, determine, and/or qualify (used interchangeably herein) aggressive prostate cancer status in a patient, including males of either African or European descent. The phrase "aggressive prostate cancer status" includes any distinguishable manifestation of the condition, including not having aggressive prostate cancer. For example, aggressive prostate cancer status includes, without limitation, the presence or absence of aggressive prostate cancer in a patient, the risk of developing aggressive prostate cancer, the stage or severity of aggressive prostate cancer, the progress of aggressive prostate cancer (e.g., progress of aggressive prostate cancer over time) and the effectiveness or response to treatment of aggressive prostate cancer (e.g., clinical follow up and surveillance of aggressive prostate cancer after treatment). Based on this status, further procedures may be indicated, including additional diagnostic tests or therapeutic procedures or regimens.

The power of a diagnostic test to correctly predict or determine status is commonly measured as the sensitivity of the assay, the specificity of the assay, or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative. Diagnostic tests that use the genes and biomarkers as identified herein may show an ROC of at least 0.6, at least about 0.7, at least about 0.8, or at least about 0.9.

The functionally related, prostate cancer driver genes and biomarkers provided above can be differentially expressed or present in non-aggressive prostate cancer or aggressive prostate cancer differentiating by the number of genes above and below a determined expression threshold number in males of either African or European descent, and, therefore, are useful in aiding in the accurate determination of aggressive prostate cancer status in these two separate patient cohorts. In certain aspects, these genes or biomarkers are measured in a patient sample using the methods described herein and compared, for example, to predefined genes or biomarkers expression thresholds and correlated to aggressive prostate cancer status. In certain aspects, the expression threshold number for each of the twenty-one functionally related, prostate cancer driver genes or biomarkers disclosed herein by race (males of African descent v. males of European descent) is specific for the assay used to measure the gene or biomarker levels/ratios.

In aspects, the expression threshold for each of the twenty-one functionally related, prostate cancer driver genes or biomarkers can be determined, for example, by measuring the amount or expression of these genes or biomarkers in a statistically significant number of samples from patients with the different aggressive prostate cancer statuses, and utilizing a defined aggressive phenotype and non-aggressive phenotype of prostate cancer in predicting prostate cancer disease aggressiveness using recursive partitioning. This results in an expression threshold number for each gene for each race, and can be used to define a high-risk and a low-risk subset for each gene for each race. The expression threshold for each of these genes will be specific to the assay used to measure the amount or expression of these genes or biomarkers, such as, e.g., DASL, genome wide or targeted RNA sequencing using whole genome microarray or target resequencing, respectively. In particular aspects, an aggressive phenotype (aggressive PCa defined as, e.g., GS≥8 or 7 (4+3), T3 disease and BCR within 3 years) and a non-aggressive phenotype (non-aggressive PCa defined as, e.g., GS≤6, T2 disease, and no BCR within 5 years), can be used to identify the expression threshold for each of the twenty-one functionally related, prostate cancer driver gene individually by race (males of African descent v. males of European descent) in predicting prostate cancer disease aggressiveness using recursive partitioning. In aspects, at least 30% of the sample is required to be in both of the daughter nodes. Therefore, for each race/gene combination, there will be a daughter node with a greater proportion of aggressive disease patients than the proportion from all samples. We denote this as the aggressive sub group Using the methods disclosed herein, the present inventors determined that for males of African descent, higher expression levels of ALOX15, BMP2, FASN, PIK3R1, PLA2G2A, and TGFB1 were associated with a more aggressive phenotype; while lower levels of ADIPOQ, AKT1, ALOX12, ALOX15B, CGA, CXCR4, CYP19A1, ERG, IL1B, IL6, IL8, NFKB1, PIK3C3, PIK3CA, and TIMP3 were associated with a more aggressive phenotype.

Therefore, in some aspects, if the genes or biomarkers comprising ADIPOQ, AKT1, ALOX12, ALOX15, BMP2, CGA, CXCR4, CYP19A1, FASN, IL1B, IL8, NFKB1, PLA2G2A TGFB1, and TIMP3 are up-regulated in a subject of African descent compared to normalized expression values (e.g. normalized gene expression values in no cancer or non-aggressive prostate cancer patients), then a measured amount(s) above the expression threshold for each gene or biomarker provides a positive indication of aggressive prostate cancer. Alternatively, if the genes or biomarkers comprising ADIPOQ, AKT1, ALOX12, ALOX15, BMP2, CGA, CXCR4, CYP19A1, FASN, IL1B, IL8, NFKB1, PLA2G2A TGFB1, and TIMP3 are down-regulated in African American males compared to normalized expression values (e.g. normalized gene expression values in no cancer or non-aggressive prostate cancer patients), then a measured amount for each gene or biomarker below the expression threshold for each gene provides a negative indication of aggressive prostate cancer. Additionally, if the genes or biomarkers comprising ALOX15B, ERG, IL6, PIK3C3, PIK3CA, and PIK3R1, are down-regulated in males of African descent compared to normalized expression values (e.g., normalized gene expression values in no cancer or non-aggressive prostate cancer patients), then a measured amount for each gene or biomarker below the expression threshold provides a positive indication of aggressive prostate cancer. Alternatively, if the gene or biomarker comprising ALOX15B, ERG, IL6, PIK3C3, PIK3CA, and PIK3R1 are up-regulated in males of African descent compared to normalized expression values (e.g., normalized gene expression values in no cancer or non-aggressive prostate cancer patients), then a measured amount for each gene or biomarker above the expression threshold provides a negative indication of aggressive prostate cancer.

Using the methods disclosed herein, the present inventors determined that for males of European descent, higher expression levels of ADIPOQ, ALOX15, CGA CXCR4, CYP19A1, IL6, IL8, NFKB1, PIK3C3, PLA2G2A, TGFB1 and TIMP3 were associated with a more aggressive phenotype; while lower levels of AKT1, ALOX12, ALOX15B, BMP2, ERG, FASN, IL1B, PIK3CA and PIK3R1 were associated with a more aggressive phenotype.

Therefore, in some aspects, if the genes or biomarkers comprising AKT1, ALOX12, ALOX15, CGA, CXCR4, CYP19A1, FASN, IL6, IL8, NFKB1, PIK3C3, PIK3CA, TGFB1, and TIMP3 are up-regulated in males of European descent compared to normalized expression values (e.g. normalized gene expression values in no cancer or non-aggressive prostate cancer patients), then a measured amount above the expression threshold for each gene or biomarker provides a positive indication of aggressive prostate cancer. Alternatively, if the genes or biomarkers comprising AKT1, ALOX12, ALOX15, CGA, CXCR4, CYP19A1, FASN, IL6, IL8, NFKB1, PIK3C3, PIK3CA, TGFB1, and TIMP3 are down-regulated in males of European descent compared to normalized expression values (e.g. normalized gene expression values in no cancer or non-aggressive prostate cancer patients), then a measured amounts below the expression threshold for each gene or biomarker provides a negative indication of aggressive prostate cancer. Additionally, if the genes or biomarkers comprising ADIPOQ, ALOX15B, BMP2, ERG, IL1B, PIK3R1, and PLA2G2A are down-regulated in males of European descent compared to normalized expression values (e.g. normalized gene expression values in no cancer or non-aggressive prostate cancer patients), then a measured amount below the optimal threshold for each gene or biomarker provides a positive indication of aggressive prostate cancer. Alternatively, if the genes or biomarkers comprising ADIPOQ, ALOX15B, BMP2, ERG, IL1B, PIK3R1, and PLA2G2A, are up-regulated in European American males compared to normalized expression values (e.g. normalized gene expression values in no cancer or non-aggressive prostate cancer patients), then a measured amount above the expression threshold for each gene or biomarker provides a negative indication of aggressive prostate cancer.

In aspects, the number of genes that a patient has that are high risk, based on comparison of the patient's gene expression compared to the expression threshold number for that particular gene, are summed to create a gene score. Recursive partitioning is again used to define a threshold for the gene score for each race, above which the patient has aggressive prostate cancer and below which the patient does not have aggressive prostate cancer. In aspects, at least 30% of the sample is required to be in both of the daughter nodes. Thus, in particular aspects, the number of genes that a patient has that are high risk may then be compared with a relevant diagnostic number of genes, cut-off(s), or multivariate model scores that distinguish a positive aggressive prostate cancer status from a negative aggressive prostate cancer status in males of African or European descent. The diagnostic number of genes represent a measured amount of the gene(s) or biomarker(s) above which or below which a patient is classified as having a particular aggressive prostate cancer status. As is well understood in the art, by adjusting the particular diagnostic cut-off(s) used in an assay, one can increase sensitivity or specificity of the diagnostic assay depending on the preference of the diagnostician. In particular aspects, the particular diagnostic cut-off can be determined, for example, by measuring the amount or expression of biomarkers in a statistically significant number of samples from patients with the different aggressive prostate cancer statuses, and drawing the cut-off to suit the desired levels of specificity and sensitivity. However, the desired cut off or threshold line to determine aggressive versus non-aggressive is that level that minimizes false positives and false negatives.

Additionally, in some aspects the risk of developing aggressive prostate cancer is determined by measuring the relevant genes or biomarkers and then either submitting them to a classification algorithm or comparing them with a reference amount, i.e., a predefined level or pattern of biomarkers that is associated with the particular risk level. In other aspects, the course of aggressive prostate cancer in a patient is determined. Aggressive prostate cancer course refers to changes in aggressive prostate cancer status over time. Over time, the amount or relative amount (e.g., the expression pattern or ratio) of the genes or biomarkers can change. Therefore, the trend of these genes or biomarkers may increase over time toward a more aggressive prostate cancer at different rates. Accordingly, this method involves measuring the level of these genes or biomarkers in a patient at different time points. The course of aggressive prostate cancer is determined based on these comparisons.

Therefore, in some aspects, a gene score is determined by adding up the positive indications of aggressive prostate cancer of the measured genes or biomarkers (e.g. comprising the twenty-one functionally related, prostate cancer driver genes or biomarkers) in a male patient of African descent (e.g. from an obtained biological sample from the patient). In some aspects, the expression level of the genes or biomarkers are measured by an appropriate assay, as described in more detail below. If the gene score for the patient is 11 or more (i.e. 11 or more of more positive indications of aggressive prostate cancer of the measured genes or biomarkers), then the patient, particularly males of African descent, is identified as likely having aggressive prostate cancer or a high risk of occurrence/recurrence of prostate cancer. In particular aspects, the resultant sensitivity and specificity of males of African descent with 11 or more positive indications of the twenty-one measured genes or biomarkers is 100% and 69%, respectively. In some aspects, if the patient is identified as likely having aggressive prostate cancer or a high risk of occurrence/recurrence of prostate cancer, then the method further comprises treating the patient with an appropriate therapeutic regimen for aggressive prostate cancer if the diagnosis of the patient correlates to aggressive prostate cancer. In other aspects, if the gene score for the patient is 10 or less (i.e. 10 or less of more positive indications of aggressive prostate cancer of the measured genes or biomarkers comprising the twenty one measured genes or biomarkers), then the patient is identified as likely having non-aggressive prostate cancer or a low risk of occurrence/recurrence of prostate cancer. In some aspects, if the patient is identified as likely having non-aggressive prostate cancer or a low risk of occurrence/recurrence of prostate cancer, then the method further comprises treating the patient with an appropriate therapeutic regimen for non-aggressive prostate cancer if the diagnosis of the patient correlates to non-aggressive prostate cancer.

In certain aspects, a gene score is determined by adding up the positive indications in the patient (e.g. from an obtained biological sample form the patient), particularly males of European descent. If the gene score for the patient is 10 or more (i.e. 10 or more positive indications of aggressive prostate cancer of the twenty-one measured genes or biomarkers), then the patient, particularly a male of European descent, is identified as likely having aggressive prostate cancer or a high risk of occurrence/recurrence of prostate cancer. In particular aspects, the resultant sensitivity and specificity of males of European descent with 10 or more positive indications of aggressive prostate cancer of the twenty one measured genes or biomarkers is 88% and 85%, respectively. In some aspects, if the patient is identified as likely having aggressive prostate cancer or a high risk of occurrence/recurrence of prostate cancer, then the method further comprises treating the patient with an appropriate therapeutic regimen for aggressive prostate cancer if the diagnosis of the patient correlates to aggressive prostate cancer. In other aspects, if the gene score for the patient is 9 or fewer (i.e. 9 or fewer of more positive indications of aggressive prostate cancer of the twenty one measured genes or biomarkers), then the patient is identified as likely having non-aggressive prostate cancer or a low risk of occurrence/recurrence of prostate cancer. In some aspects, if the patient is identified as likely having non-aggressive prostate cancer or a low risk of occurrence/recurrence of prostate cancer, then the method further comprises treating the patient with an appropriate therapeutic regimen for non-aggressive prostate cancer if the diagnosis of the patient correlates to non-aggressive prostate cancer.

As such, in aspects, a method for identifying a male of African descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; and c) determining the expression threshold level for each prostate cancer driver gene in step b. In aspects, determining the expression threshold level for each gene comprises: 1) measuring the amount or expression of each prostate cancer drive gene in step b or biomarkers in a statistically significant number of samples from male patients of African descent with the different aggressive prostate cancer statuses; and 2) utilizing a defined aggressive phenotype and non-aggressive phenotype of prostate cancer in predicting prostate cancer disease aggressiveness using recursive partitioning; d) determining a number of positive indications for aggressive prostate cancer by comparing the detected expression levels of each gene determined in step b) to the expression threshold level for each determined in step c) for each gene. The method further comprises the steps of: e) determining a gene score threshold using recursive partitioning; and f) identifying the patient as having or likely to have aggressive prostate cancer if there are more positive indications then the gene score threshold determined in step e).

In certain aspects of a method for identifying a male of African descent as having or likely to have aggressive prostate cancer, the aggressive phenotype comprises a Gleason score of greater than or equal to 8 or 7 (4+3), T3 disease and BCR within 3 years. In aspects of method for identifying a male of African descent as having or likely to have aggressive prostate cancer the non-aggressive phenotype comprises a Gleason score of less than or equal to 6, T2 disease, and no BCR within 5 years.

In certain aspects of a method for identifying a male of African descent as having or likely to have aggressive prostate cancer, the recursive partitioning of step c) 2) comprises two daughter nodes. In some aspects, the daughter nodes of the recursive partitioning of step c) 2) require at least 30% of the sample to be in both daughter nodes. In certain aspects, the recursive partitioning step of step e) comprises two daughter nodes. In some aspects, the daughter nodes of the recursive partitioning of step e) require at least 30% of the sample to be in both daughter nodes.

In certain aspects of a method for identifying a male of African descent as having or likely to have aggressive prostate cancer, determining the number of positive indications comprises determining if ADIPOQ, AKT1, ALOX12, ALOX15, BMP2, CGA, CXCR4, CYP19A1, FASN, IL1B, IL8, NFKB1, PLA2G2A TGFB1, and TIMP3 are upregulated in the biological sample to a level greater than the expression threshold level for each gene and determining if ALOX15B, ERG, IL6, PIK3C3, PIK3CA, and PIK3R1 are down regulated in the biological sample to a level less than the expression threshold level for each gene.

In certain aspects of a method for identifying a male of African descent as having or likely to have aggressive prostate cancer, the method further comprises identifying the patient as having or likely to have nonaggressive prostate cancer if there are there are fewer positive indications then the gene score threshold determined in step e).

In certain aspects of a method for identifying a male of African descent as having or likely to have aggressive prostate cancer, the gene threshold score is eleven.

In certain aspects of a method for identifying a male of African descent as having or likely to have aggressive prostate cancer, wherein the biological sample is a tumor biopsy.

In certain aspects of a method for identifying a male of African descent as having or likely to have aggressive prostate cancer, the step of detecting comprises PCR, DASL, genome wide RNA sequencing, targeted RNA sequencing, or an immunoassay.

In certain aspects of a method for identifying a male of African descent as having or likely to have aggressive prostate cancer, the method further comprises treating the patient with an appropriate therapeutic regimen for aggressive prostate cancer if the diagnosis of the patient correlates to aggressive prostate cancer or treating the patient with an appropriate therapeutic regimen for non-aggressive prostate cancer if the diagnosis of the patient correlates to non-aggressive prostate cancer.

In other aspects, a method for identifying a male of European descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; and c) determining the expression threshold level for each prostate cancer driver gene in step b. In aspects, determining the expression threshold level for each gene comprises: 1) measuring the amount or expression of each prostate cancer drive gene in step b or biomarkers in a statistically significant number of samples from male patients of European descent with the different aggressive prostate cancer statuses; and 2) utilizing a defined aggressive phenotype and non-aggressive phenotype of prostate cancer in predicting prostate cancer disease aggressiveness using recursive partitioning; d) determining a number of positive indications for aggressive prostate cancer by comparing the detected expression levels of each gene determined in step b) to the expression threshold level for each determined in step c) for each gene. The method further comprises the steps of: e) determining a gene score threshold using recursive partitioning; and f) identifying the patient as having or likely to have aggressive prostate cancer if there are more positive indications then the gene score threshold determined in step e).

In certain aspects of a method for identifying a male of European descent as having or likely to have aggressive prostate cancer, the aggressive phenotype comprises a Gleason score of greater than or equal to 8 or 7 (4+3), T3 disease and BCR within 3 years. In aspects of method for identifying a male of European descent as having or likely to have aggressive prostate cancer the non-aggressive phenotype comprises a Gleason score of less than or equal to 6, T2 disease, and no BCR within 5 years.

In certain aspects of a method for identifying a male of European descent as having or likely to have aggressive prostate cancer, the recursive partitioning of step c) 2) comprises two daughter nodes. In some aspects, the daughter nodes of the recursive partitioning of step c) 2) require at least 30% of the sample to be in both daughter nodes. In certain aspects, the recursive partitioning step of step e) comprises two daughter nodes. In some aspects, the daughter nodes of the recursive partitioning of step e) require at least 30% of the sample to be in both daughter nodes.

In certain aspects of a method for identifying a male of European descent as having or likely to have aggressive prostate cancer, determining the number of positive indications comprises determining if AKT1, ALOX12, ALOX15, CGA, CXCR4, CYP19A1, FASN, IL6, IL8, NFKB1, PIK3C3, PIK3CA, TGFB1, and TIMP3 are upregulated in the biological sample to a level greater than the expression threshold level for each gene and determining if at least one or more of ADIPOQ, ALOX15B, BMP2, ERG, IL1B, PIK3R1, and PLA2G2A are down regulated in the biological sample to a level less than the expression threshold level for each gene.

In certain aspects of a method for identifying a male of European descent as having or likely to have aggressive prostate cancer, the method further comprises identifying the patient as having or likely to have nonaggressive prostate cancer if there are there are fewer positive indications then the gene score threshold determined in step e).

In certain aspects of a method for identifying a male of European descent as having or likely to have aggressive prostate cancer, the gene threshold score is ten.

In certain aspects of a method for identifying a male of European descent as having or likely to have aggressive prostate cancer, wherein the biological sample is a tumor biopsy.

In certain aspects of a method for identifying a male of European descent as having or likely to have aggressive prostate cancer, the step of detecting comprises PCR, DASL, genome wide RNA sequencing, targeted RNA sequencing, or an immunoassay.

In certain aspects of a method for identifying a male of European descent as having or likely to have aggressive prostate cancer, the method further comprises treating the patient with an appropriate therapeutic regimen for aggressive prostate cancer if the diagnosis of the patient correlates to aggressive prostate cancer or treating the patient with an appropriate therapeutic regimen for non-aggressive prostate cancer if the diagnosis of the patient correlates to non-aggressive prostate cancer.

In further aspects, a method for identifying a male of African descent as having or likely to have aggressive prostate cancer is provided. In some aspects, the methods comprise the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; c) determining a number of positive indications for aggressive prostate cancer by comparing the detected expression levels of each of the prostate cancer driver genes determined in step b to an expression threshold level for each prostate cancer driver gene; and d) identifying the patient as having or likely to have aggressive prostate cancer if there are more positive indications then a gene score threshold.

In other aspects, a method for identifying a male patient of European descent as having or likely to have aggressive prostate cancer is provided. In some aspects, the method comprises the steps of: a) obtaining a biological sample from the patient; b) detecting expression levels in the biological sample of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3; c) determining a number of positive indications for aggressive prostate cancer by comparing the detected expression levels of each of the prostate cancer driver genes determined in step b to an expression threshold level for each prostate cancer driver gene; and d) identifying the patient as having or likely to have aggressive prostate cancer if there are more positive indications then a gene score threshold.

An appropriate regimen for aggressive or non-aggressive prostate cancer may include or exclude surgery, radiation therapy, cryosurgery, hormone therapy, chemotherapy, bone directed treatment, monitoring, or combinations thereof.

Surgery is a common choice to try to cure prostate cancer if it is not thought to have spread outside the gland (stage T1 or T2 cancers). The main type of surgery for prostate cancer is known as a radical prostatectomy. In this operation, the surgeon removes the entire prostate gland plus some of the tissue around it, including the seminal vesicles. Side effects of surgery include incontinence (stress, overflow or urge), erectile dysfunction, loss of fertility, lymphedema and inguinal hernia.

Radiation therapy uses high-energy rays or particles to kill cancer cells. Radiation may be used:
  As the first treatment for low-grade cancer that is still just in the prostate gland. Cure rates for men with these types of cancers are about the same as those for men getting radical prostatectomy.
  As part of the first treatment (along with hormone therapy) for cancers that have grown outside of the prostate gland and into nearby tissues.
  If the cancer is not removed completely or comes back (recurs) in the area of the prostate after surgery.
  If the cancer is advanced, to reduce the size of the tumor and to provide relief from present and possible future symptoms. The 2 main types of radiation therapy are external beam radiation and brachytherapy (internal radiation). Both appear to be good methods of treating prostate cancer, although there is more long-term information about the results with external beam radiation.

Cryosurgery (also called cryotherapy or cryoablation) is sometimes used to treat early-stage prostate cancer by freezing it. Most doctors do not use cryosurgery as the first treatment for prostate cancer, but it is sometimes an option if the cancer has come back after other treatments. As with brachytherapy, this may not be a good option for men with large prostate glands. In this approach, the doctor uses transrectal ultrasound (TRUS) to guide several hollow probes (needles) through the skin between the anus and scrotum and into the prostate. This type of procedure requires spinal or epidural anesthesia (where the lower half of your body is numbed) or general anesthesia. Very cold gases are then passed through the needles, creating ice balls that destroy the prostate. To be sure the prostate is destroyed without too much damage to nearby tissues, the doctor carefully watches the ultrasound images during the procedure. Warm saltwater is circulated through a catheter in the urethra during the procedure to keep it from freezing. The catheter is kept in place for about 3 weeks afterward to allow the bladder to empty in recovery.

Hormone therapy is also called androgen deprivation therapy (ADT) or androgen suppression therapy. The goal is to reduce levels of male hormones, called androgens, in the body, or to stop them from affecting prostate cancer cells. The main androgens are testosterone and dihydrotestosterone (DHT). Most of the body's androgens come from the testicles, but the adrenal glands also make a small amount. Androgens stimulate prostate cancer cells to grow. Lowering androgen levels or stopping them from getting into prostate cancer cells often makes prostate cancers shrink or grow more slowly for a time. But hormone therapy alone does not cure prostate cancer. Hormone therapies include the following:
  Degarelix (Firmagon) is an LHRH antagonist. LHRH antagonists work like LHRH agonists, but they reduce testosterone levels more quickly and do not cause tumor flare like the LHRH agonists do.
  Abiraterone (Zytiga) blocks an enzyme called CYP17, which helps stop prostate, liver, adrenals and other cells from making androgens.
  Enzalutamide (Xtandi) is a newer type of anti-androgen. When androgens bind to the androgen receptor, the receptor sends a signal to the cell's control center, telling it to grow and divide. Enzalutamide blocks this signal.

For prostate cancer chemotherapy, chemo drugs are typically used one at a time. Some of the chemo drugs used to treat prostate cancer include:

Docetaxel (Taxotere®)
Cabazitaxel (Jevtana®)
Mitoxantrone (Novantrone®)
Estramustine (Emcyt®)
Doxorubicin (Adriamycin®)
Etoposide (VP-16)
Vinblastine (Velban®)
Paclitaxel (Taxol®)
Carboplatin (Paraplatin®)
Vinorelbine (Navelbine®)

In most cases, the first chemo drug given is docetaxel, combined with the steroid drug prednisone. If this drug does not work (or stops working), cabazitaxel is often the next chemo drug tried (although there may be other treatment options as well). Both of these drugs have been shown to help men live several months longer, on average, than older chemo drugs. They may slow the cancer's growth and also reduce symptoms, resulting in a better quality of life. Still, chemotherapy is very unlikely to cure prostate cancer.

For bone directed treatments, if prostate cancer grows outside of the prostate gland itself, it often first grows into nearby tissues or spreads to nearby lymph nodes. After this, prostate cancer nearly always spreads to the bones. Bone metastasis can be painful and can cause other problems, such as fractures (breaks) or high blood calcium levels, which can be dangerous or even life threatening.

If the cancer has grown outside the prostate, preventing or slowing the spread of the cancer to the bones is a major goal of treatment. If the cancer has already reached the bones, controlling or relieving pain and other complications is also a very important part of treatment.

In certain aspects, the genes or biomarkers of the present disclosure can be detected/measured/quantified by polymerase chain reaction (PCR). PCR can include quantitative type PCR, such as quantitative, real-time PCR (both singleplex and multiplex). In certain aspects, the quantitation steps are carried using quantitative, real-time PCR. Primers that specifically bind and amplify one or more biomarkers described herein can be designed using the publicly available sequences thereof.

In other aspects, the genes or biomarkers of the present disclosure can be detected and/or measured by immunoassay. Immunoassay requires biospecific capture reagents, such as antibodies, to capture and/or detect the presence of or level of one or more biomarkers. Many antibodies to each of the target markers analyzed herein are available commercially. Antibodies also can be produced by methods well known in the art, e.g., by immunizing animals with an immunogen correlating or corresponding to a target biomarker. Biomarkers can be isolated from samples based on their binding characteristics. Alternatively, if the amino acid sequence of a polypeptide biomarker is known, the polypeptide can be synthesized and used to generate antibodies by methods well-known in the art.

The present disclosure contemplates use of traditional immunoassays including, for example, sandwich immunoassays including ELISA or fluorescence-based immunoassays, immunoblots, western blots (WB), as well as other enzyme immunoassays, such as nephelometry, and SELDI-based immunoassay. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry. Additionally, in some aspects cDNA-mediated annealing, selection, extension and ligation (DASL) can be used.

Although antibodies are useful because of their extensive characterization, any other suitable agent (e.g., a peptide, an aptamer, or a small organic molecule) that specifically binds a biomarker of the present invention is optionally used in place of the antibody in an appropriate assay as known in the art for detection and/or quantitation of a biomarker. For example, an aptamer that specifically binds a biomarker and/or one or more of its breakdown products may be used.

In other aspect of the present disclosure, kits for qualifying prostate cancer status are provided. The kits are used to detect the biomarkers described herein. In a specific aspect, the kit is provided as a PCR kit comprising primers that specifically bind to one or more of the biomarkers described herein. One of ordinary skill in the art can design primers the specifically bind and amplify the target genes and biomarkers described herein comprising at least one of ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A TGFB1, and TIMP3. ALOX15B, ERG, IL6, PIK3C3, PIK3CA, and PIK3R1. The kit can further comprise substrates and other reagents necessary for conducting PCR (e.g., quantitative real-time PCR). The kit can be configured to conduct singleplex or multiplex PCR. The kit can further comprise instructions for carrying out the PCR reaction(s).

In other aspects, the kit is provided as an ELISA kit comprising antibodies to the biomarker(s) of the present invention. In a specific aspect, the antibodies specifically bind to a biomarker including at least one of ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A TGFB1, and TIMP3. ALOX15B, ERG, IL6, PIK3C3, PIK3CA, and PIK3R1. The ELISA kit may comprise a solid support, such as a chip, microtiter plate (e.g., a 96-well plate), bead, or resin having biomarker capture reagents attached thereon. The kit may further comprise a means for detecting the biomarker(s), such as antibodies, and a secondary antibody-signal complex such as horseradish peroxidase (HRP)-conjugated goat anti-rabbit IgG antibody and tetramethyl benzidine (TMB) as a substrate for HRP.

In some aspects, a patient can be diagnosed by adding a biological sample such a needle biopsy from a tumor, or other biological sample from the patient, to the kit and detecting the relevant biomarker(s) conjugated with antibodies, specifically, by a method which comprises the steps of: (i) collecting a blood sample from the patient; (ii) separating blood serum from the patient's blood; (iii) adding the blood serum from patient to a diagnostic kit; and, (iv) detecting the biomarker(s) conjugated with antibodies. In this method, the antibodies are brought into contact with the patient's serum. If the biomarkers are present in the sample, the antibodies will bind to the sample, or a portion thereof. In other kit and diagnostic aspects, a biological sample need not be collected from the patient (i.e., it is already collected). Moreover, in other aspects, the sample may include a tissue sample or other clinical sample.

The kit can also include a washing solution or instructions for making a washing solution, in which the combination of the capture reagents and the washing solution allows capture of the biomarkers on the solid support for subsequent detection by, e.g., antibodies or mass spectrometry. In some aspects, a kit can include instructions for suitable operational parameters in the form of a label or separate insert. For example, the instructions may inform a consumer about how to collect the sample, how to wash the probe or the particular biomarkers to be detected, etc. In some aspects, the kit can include one or more containers with biomarker samples, to be used as standard(s) for calibration.

In order that various aspects may be more readily understood, reference is made to the following examples which are intended to illustrate various embodiments, but do not limit the scope thereof.

EXAMPLES

To derive a gene score, the investigators examined twenty-one functionally related, prostate cancer driver genes that had a statistically significant difference in expression in males of African descent and males of European descent: ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3. Utilizing the aggressive and nonaggressive phenotypes as follows: aggressive prostate cancer includes GS=8 or 7 (4+3), T3 disease and BCR within 3 years; non-aggressive prostate cancer includes GS=6, T2 disease, and no BCR within 5 years, the expression threshold for each gene individually by race was identified in predicting disease aggressiveness using recursive partitioning, requiring at least 30% of the sample to be in both of the daughter nodes. This resulted in a high-risk and a low-risk subset for each gene for each race. Link to online database for the data generated from the DASL assay used for determining the expression thresholds for each gene by race: http://www.ncbi.nlm.nih.gov/geo/query/acc.cgi?acc=GSE41968.

For males of African descent, if the genes or biomarkers comprising ADIPOQ, AKT1, ALOX12, ALOX15, BMP2, CGA, CXCR4, CYP19A1, FASN, IL1B, IL8, NFKB1, PLA2G2A TGFB1, and TIMP3 are up-regulated compared to normalized expression values (e.g. normalized gene expression values in no cancer or non-aggressive prostate cancer patients), then a measured amount(s) above the expression threshold for each gene or biomarker provides a positive indication of aggressive prostate cancer. Additionally, if the genes or biomarkers comprising ALOX15B, ERG, IL6, PIK3C3, PIK3CA, and PIK3R1, are down-regulated in males of African descent compared to normalized expression values (e.g., normalized gene expression values in no cancer or non-aggressive prostate cancer patients), then a measured amount for each gene or biomarker below the expression threshold provides a positive indication of aggressive prostate cancer. The expression thresholds for each of these twenty-one genes in males of African descent using the DASL assay are disclosed in Table 1. FIG. 1 depicts the recursive partitioning used to determine the expression threshold for ADIPOQ in males of African descent.

For males of European descent, if the genes or biomarkers comprising AKT1, ALOX12, ALOX15, CGA, CXCR4, CYP19A1, FASN, IL6, IL8, NFKB1, PIK3C3, PIK3CA, TGFB1, and TIMP3 are up-regulated compared to normalized expression values (e.g. normalized gene expression values in no cancer or non-aggressive prostate cancer patients), then a measured amount above the expression threshold for each gene or biomarker provides a positive indication of aggressive prostate cancer. Additionally, if the genes or biomarkers comprising ADIPOQ, ALOX15B, BMP2, ERG, IL1B, PIK3R1, and PLA2G2A are down-regulated in males of European descent compared to normalized expression values (e.g. normalized gene expression values in no cancer or non-aggressive prostate cancer patients), then a measured amount below the expression threshold for each gene or biomarker provides a positive indication of aggressive prostate cancer. The expression thresholds for each of these twenty-one genes in males of European descent using the DASL assay are disclosed in Table 1.

Figure 2:
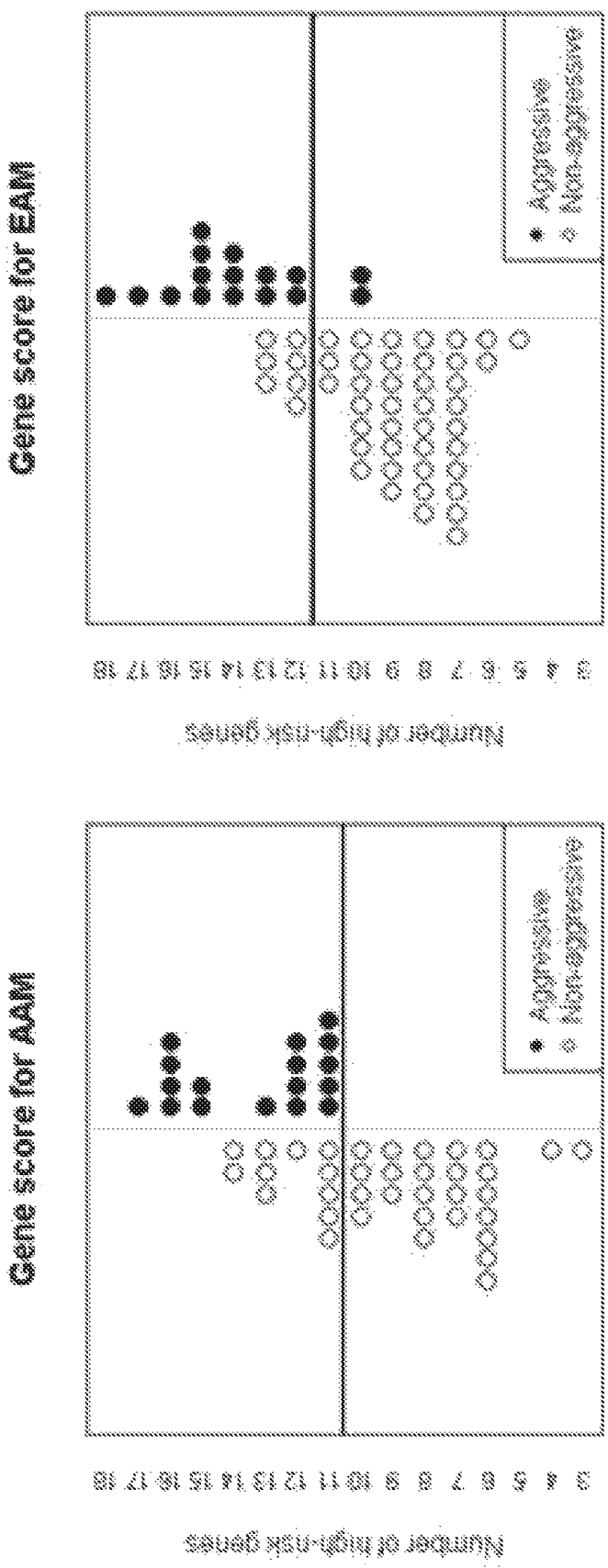
FIG. 2 depicts an illustration of gene score mechanism for males of African descent (AAM) and males of European descent (EAM) based on results of microarray gene expression analysis. The number of genes that a patient has that are high risk are summed to create a gene score. In this illustration race-specific thresholds for prostate cancer aggressiveness and treatment decision can be determined: if an AAM patient had at least 11 of 21 genes that were high-risk or an EAM patient had at least 12 of 21 genes that were high-risk
Figure 3:
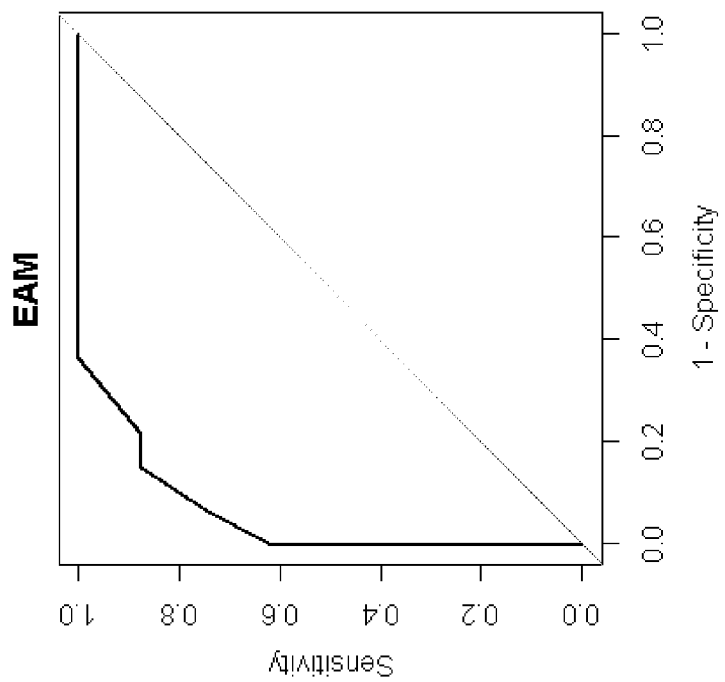
FIG. 3 depicts ROC curves of gene scores created from the DASL database for males of African descent (AAM) and males of European descent (EAM).
Figure 3:
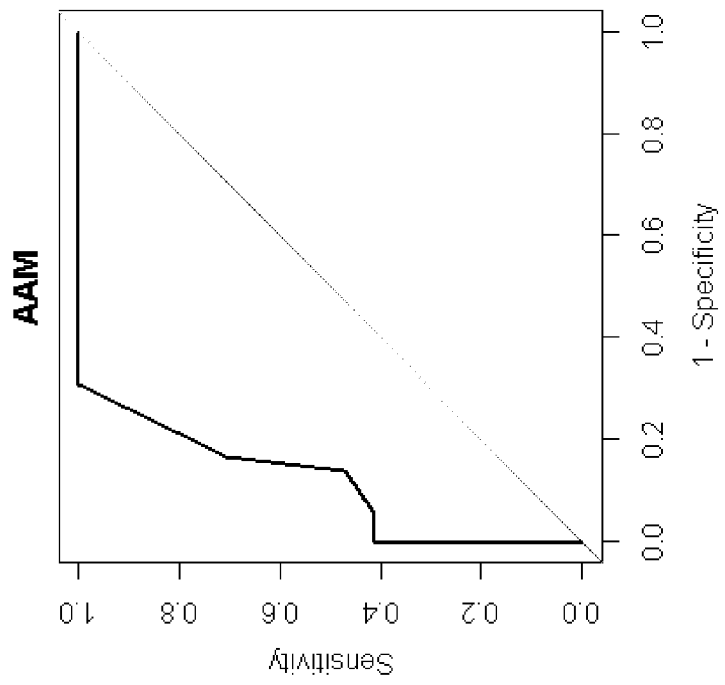

Subsequently, the number of genes that a patient has that are high risk (e.g., provides a positive indication of cancer based on the expression threshold determined for the specific assay used) are summed to create a gene score. Recursive partitioning is again used to define a threshold for the gene score for each race. FIG. 2 is an illustration of gene score mechanism. These gene scores for males of African descent and males of European descent are based on the results of DASL microarray gene expression analysis. In this example race-specific thresholds for prostate cancer aggressiveness and treatment decision can be determined: if an a male patient of African descent had at least 11 of 21 genes that were high-risk they were determined to have aggressive prostate cancer, while if a male patient of European descent had at least 12 of 21 genes that were high-risk they were determined to have aggressive prostate cancer. Using the DASL assay, the resultant sensitivity and specificity for males of African descent with 11 or more high risk genes is 100% and 69%, respectively. The resultant sensitivity and specificity for males of European descent with 10 or more high risk genes is 88% and 85%, respectively. The corresponding ROC curves shown in FIG. 3, illustrate that even with a small number of genes, a reasonably good classifier for disease aggressiveness can be created.

Definition of high risk subset for each gene and race. For example for ADIPOQ, normalized gene expression values>−3.343 for males of African descent are predicted to be aggressive; while for males of European descent normalized gene expression values<−3.322 are predicted to be aggressive.

TABLE 1

Determined expression thresholds for the twenty-one functionally related, prostate cancer driver gene in males of African descent and males of European descent using the DASL assay.

| | Gene | AAM.dir | AAM.cutpt | EAM.dir | EAM.cutpt |
|---|---|---|---|---|---|
| 1 | ADIPOQ | > | −3.343 | < | −3.322 |
| 2 | AKT1 | > | −1.687 | > | −1.707 |
| 3 | ALOX12 | > | −4.034 | > | −4.038 |
| 4 | ALOX15 | > | −3.463 | > | −3.479 |
| 5 | ALOX15B | < | −0.400 | < | −0.679 |
| 6 | BMP2 | > | −2.327 | < | −2.985 |
| 7 | CGA | > | −4.063 | > | −4.658 |
| 8 | CXCR4 | > | −0.422 | > | −0.505 |
| 9 | CYP19A1 | > | −4.027 | > | −4.523 |
| 10 | ERG | < | −2.270 | < | −2.005 |
| 11 | FASN | > | −0.496 | > | −0.197 |
| 12 | IL1B | > | −1.354 | < | −1.974 |
| 13 | IL6 | < | −0.722 | > | −1.516 |
| 14 | IL8 | > | −0.596 | > | −1.201 |
| 15 | NFKB1 | > | −0.228 | > | −0.174 |
| 16 | PIK3C3 | < | −0.053 | > | −0.058 |
| 17 | PIK3CA | < | −0.247 | > | −0.197 |
| 18 | PIK3R1 | < | 0.238 | < | 0.625 |
| 19 | PLA2G2A | > | 1.211 | < | 1.199 |
| 20 | TGFB1 | > | −0.196 | > | −0.285 |
| 21 | TIMP3 | > | −3.551 | > | −3.407 |

The invention claimed is:

1. A method for treating a patient of African descent or European descent having or likely to have aggressive prostate cancer comprising the steps of:
   a) detecting expression levels in a biological sample from the patient of a group of prostate cancer driver genes, said genes comprising ADIPOQ, AKT1, ALOX12, ALOX15, ALOX15B, BMP2, CGA, CXCR4, CYP19A1, ERG, FASN, IL1B, IL6, IL8, NFKB1, PIK3C3, PIK3CA, PIK3R1, PLA2G2A, TGFB1, and TIMP3;
   b) determining a number of positive indications for aggressive prostate cancer by comparing the detected expression levels of each of the prostate cancer driver genes determined in step a) to an expression threshold level for each prostate cancer driver gene wherein the expression threshold level for each gene is determined by: 1) measuring the amount or expression of each prostate cancer gene in step a) in a statistically significant number of samples from patients of African descent or European descent with different aggressive prostate cancer statuses; and 2) utilizing a defined aggressive phenotype and non-aggressive phenotype of prostate cancer in predicting prostate cancer disease aggressiveness using recursive partitioning, wherein the recursive partitioning comprises two daughter nodes, wherein the daughter nodes require at least 30% of the sample to be in both of the daughter nodes; and
   c) identifying the patient as having or likely to have aggressive prostate cancer when there are more positive indications than a gene score threshold; and
   d) treating the patient identified in step c) by surgical removal of the cancer.

2. The method of claim 1 further comprising obtaining the biological sample from the patient prior to said step of detecting.

3. The method of claim 1, wherein the biological sample is a tumor biopsy.

4. A method of claim 1, when the step of detecting comprises PCR, DASL, genome-wide RNA sequencing, targeted RNA sequencing, an immunoassay, or any combination thereof.

5. The method of claim 1, wherein determining the number of positive indications comprises determining if ADIPOQ, AKT1, ALOX12, ALOX15, BMP2, CGA, CXCR4, CYP19A1, FASN, IL1B, IL8, NFKB1, PLA2G2A TGFB1, and TIMP3 are upregulated in the biological sample to a level greater than the expression threshold level for each gene and determining if ALOX15B, ERG, IL6, PIK3C3, PIK3CA, and PIK3R1 are down regulated in the biological sample to a level less than the expression threshold level for each gene.

6. The method of claim 1, wherein the patient is of African descent and the method further comprises identifying the patient as having or likely to have aggressive prostate cancer when there are 11 or more positive indications.

7. The method of claim 1, wherein the patient is of European descent and the method further comprises identifying the patient as having or likely to have aggressive prostate cancer when there are 10 or more positive indications.

8. The method of claim 1, wherein, prior to detecting expression levels in a biological sample from the patient, the patient was subjected to prior treatment for prostate cancer, and wherein the aggressive phenotype comprises a Gleason score of greater than or equal to 8 or 7 (4+3), T3 disease and BCR within 3 years of the prior treatment.

9. The method of claim 1, wherein, prior to detecting expression levels in a biological sample from the patient, the patient was subjected to prior treatment for prostate cancer, and wherein the non-aggressive phenotype comprises a Gleason score of less than or equal to 6, T2 disease, and no BCR within 5 years of the prior treatment.

* * * * *